United States Patent
Palasis et al.

(10) Patent No.: US 8,540,765 B2
(45) Date of Patent: *Sep. 24, 2013

(54) MEDICAL IMPLANT

(75) Inventors: Maria Palasis, Wellesley, MA (US); Chang Cheng You, Burlington, MA (US); Daniel Concagh, Medfield, MA (US); Lee Core, Needham, MA (US); Kicherl Ho, Groton, MA (US); Upma Sharma, Somerville, MA (US); Greg Zugates, Chelmsford, MA (US)

(73) Assignee: 480 Biomedical, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,025

(22) Filed: Feb. 9, 2012

(65) Prior Publication Data

US 2012/0143300 A1    Jun. 7, 2012

Related U.S. Application Data

(63) Continuation of application No. 13/183,104, filed on Jul. 14, 2011, which is a continuation-in-part of application No. 12/783,261, filed on May 19, 2010, now Pat. No. 8,137,396.

(60) Provisional application No. 61/179,834, filed on May 20, 2009, provisional application No. 61/227,308, filed on Jul. 21, 2009, provisional application No. 61/251,984, filed on Oct. 15, 2009.

(51) Int. Cl.
   *A61F 2/06*    (2013.01)

(52) U.S. Cl.
   USPC .................................. 623/1.38; 623/1.46

(58) Field of Classification Search
   USPC ...... 623/1.11–1.23, 1.38–1.54; 606/191–195
   See application file for complete search history.

(56) References Cited

U.S. PATENT DOCUMENTS

| | | | | |
|---|---|---|---|---|
| 4,243,775 A | * | 1/1981 | Rosensaft et al. | 525/415 |
| 4,300,565 A | * | 11/1981 | Rosensaft et al. | 606/224 |
| 4,351,069 A | * | 9/1982 | Ballintyn et al. | 623/23.36 |
| 4,461,298 A |   | 7/1984 | Shalaby et al. | |
| 4,643,734 A | * | 2/1987 | Lin | 528/354 |
| 4,916,193 A |   | 4/1990 | Tang et al. | |

(Continued)

FOREIGN PATENT DOCUMENTS

| | | |
|---|---|---|
| EP | 1308473 | 5/2003 |
| EP | 0724436 | 1/2004 |

(Continued)

OTHER PUBLICATIONS

Hietala et al., "Platelet deposition on stainless steel, spiral and braided polylactide stents", Thrombosis and Haemostatis, vol. 92(6):1394-1401, (2004).

(Continued)

*Primary Examiner* — Alvin J. Stewart
(74) *Attorney, Agent, or Firm* — Bingham McCutchen LLP

(57) ABSTRACT

Disclosed is a self-expanding medical implant for placement within a lumen of a patient. The implant comprises a woven or non-woven structure having a substantially tubular configuration, and is designed to be low-profile such that it is deliverable with a small diameter catheter. The implant has a high recoverability and desired mechanical properties.

25 Claims, 7 Drawing Sheets

(56) References Cited

U.S. PATENT DOCUMENTS

| | | | | |
|---|---|---|---|---|
| 4,920,203 | A | 4/1990 | Tang et al. | |
| 4,990,158 | A * | 2/1991 | Kaplan et al. | 623/1.38 |
| 5,066,772 | A | 11/1991 | Tang et al. | |
| 5,145,945 | A | 9/1992 | Tang et al. | |
| 5,185,408 | A | 2/1993 | Tang et al. | |
| 5,213,580 | A * | 5/1993 | Slepian et al. | 128/898 |
| 5,256,764 | A | 10/1993 | Tang et al. | |
| 5,274,074 | A | 12/1993 | Tang et al. | |
| 5,356,423 | A | 10/1994 | Tihon | |
| 5,412,068 | A | 5/1995 | Tang et al. | |
| 5,449,372 | A | 9/1995 | Schmaltz et al. | |
| 5,486,593 | A | 1/1996 | Tang et al. | |
| 5,516,781 | A | 5/1996 | Morris | |
| 5,531,735 | A * | 7/1996 | Thompson | 604/891.1 |
| 5,534,287 | A * | 7/1996 | Lukic | 427/2.25 |
| 5,562,725 | A | 10/1996 | Schmitt | |
| 5,563,146 | A | 10/1996 | Morris | |
| 5,595,751 | A * | 1/1997 | Bezwada et al. | 424/422 |
| 5,616,608 | A | 4/1997 | Kinsella | |
| 5,634,946 | A * | 6/1997 | Slepian | 128/898 |
| 5,650,447 | A | 7/1997 | Keefer | |
| 5,665,077 | A | 9/1997 | Rosen | |
| 5,665,728 | A | 9/1997 | Morris | |
| 5,676,963 | A | 10/1997 | Keefer | |
| 5,703,200 | A | 12/1997 | Bezwada | |
| 5,716,981 | A | 2/1998 | Hunter | |
| 5,733,925 | A | 3/1998 | Kunz | |
| 5,741,325 | A | 4/1998 | Chaikof | |
| 5,762,625 | A | 6/1998 | Igaki | |
| 5,766,710 | A | 6/1998 | Turnlund | |
| 5,788,979 | A | 8/1998 | Altschuler | |
| 5,797,877 | A | 8/1998 | Hamilton et al. | |
| 5,797,887 | A * | 8/1998 | Rosen et al. | 604/265 |
| 5,799,384 | A | 9/1998 | Schwartz et al. | |
| 5,824,053 | A | 10/1998 | Khosravi | |
| 5,834,582 | A | 11/1998 | Sinclair | |
| 5,851,217 | A | 12/1998 | Wolff | |
| 5,871,535 | A | 2/1999 | Wolff | |
| 5,899,935 | A | 5/1999 | Ding | |
| 5,968,091 | A | 10/1999 | Pinchuk et al. | |
| 5,984,957 | A | 11/1999 | Laptewicz | |
| 5,993,972 | A | 11/1999 | Reich et al. | |
| 5,994,444 | A | 11/1999 | Trescony | |
| 5,997,468 | A | 12/1999 | Wolff et al. | |
| 6,004,346 | A | 12/1999 | Wolff et al. | |
| 6,004,573 | A * | 12/1999 | Rathi et al. | 424/426 |
| 6,005,020 | A | 12/1999 | Loomis | |
| 6,051,021 | A | 4/2000 | Frid | |
| 6,074,659 | A | 6/2000 | Kunz | |
| 6,074,660 | A * | 6/2000 | Jamiolkowski et al. | 424/426 |
| 6,083,257 | A | 7/2000 | Taylor | |
| 6,083,524 | A * | 7/2000 | Sawhney et al. | 424/426 |
| 6,087,479 | A | 7/2000 | Stamler | |
| 6,117,949 | A * | 9/2000 | Rathi et al. | 525/415 |
| 6,120,536 | A | 9/2000 | Ding | |
| 6,135,791 | A | 10/2000 | Wang et al. | |
| 6,143,829 | A * | 11/2000 | Babb et al. | 525/194 |
| 6,153,252 | A | 11/2000 | Hossainy et al. | |
| 6,161,399 | A | 12/2000 | Jayaraman | |
| 6,171,232 | B1 | 1/2001 | Papandrecu | |
| 6,171,609 | B1 | 1/2001 | Kunz | |
| 6,179,051 | B1 | 1/2001 | Ayub | |
| 6,193,746 | B1 | 2/2001 | Strecker | |
| 6,207,767 | B1 | 3/2001 | Bennett et al. | |
| 6,221,100 | B1 | 4/2001 | Strecker | |
| 6,221,997 | B1 * | 4/2001 | Woodhouse et al. | 528/61 |
| 6,232,434 | B1 | 5/2001 | Stamler | |
| 6,238,687 | B1 * | 5/2001 | Mao et al. | 424/426 |
| 6,240,978 | B1 | 6/2001 | Gianotti | |
| 6,245,103 | B1 | 6/2001 | Stinson | |
| 6,249,952 | B1 | 6/2001 | Ding | |
| 6,261,594 | B1 | 7/2001 | Smith | |
| 6,268,390 | B1 | 7/2001 | Kunz | |
| 6,270,779 | B1 | 8/2001 | Fitzhugh | |
| 6,284,305 | B1 | 9/2001 | Ding | |
| 6,290,722 | B1 | 9/2001 | Wang | |
| 6,295,714 | B1 | 10/2001 | Roychowdhury | |
| 6,299,604 | B1 | 10/2001 | Ragheb | |
| 6,299,636 | B1 | 10/2001 | Schmitt | |
| 6,306,421 | B1 | 10/2001 | Kunz | |
| 6,342,068 | B1 | 1/2002 | Thompson | |
| 6,359,073 | B1 * | 3/2002 | Babb et al. | 525/194 |
| 6,368,346 | B1 | 4/2002 | Jadhav | |
| 6,375,787 | B1 * | 4/2002 | Lukic | 156/294 |
| 6,379,691 | B1 | 4/2002 | Tedeschi | |
| 6,403,635 | B1 | 6/2002 | Kinsella | |
| 6,403,759 | B2 | 6/2002 | Stamler | |
| 6,419,694 | B1 | 7/2002 | Sandock | |
| 6,423,092 | B2 | 7/2002 | Datta | |
| 6,429,232 | B1 | 8/2002 | Kinsella | |
| 6,451,337 | B1 | 9/2002 | Smith | |
| 6,471,978 | B1 | 10/2002 | Stamler | |
| 6,488,701 | B1 | 12/2002 | Nolting et al. | |
| 6,488,705 | B2 | 12/2002 | Schmitt | |
| 6,488,951 | B2 | 12/2002 | Toone | |
| 6,500,203 | B1 | 12/2002 | Thompson et al. | |
| 6,506,411 | B2 | 1/2003 | Hunter | |
| 6,514,515 | B1 * | 2/2003 | Williams | 424/424 |
| 6,515,009 | B1 | 2/2003 | Kunz | |
| 6,537,312 | B2 | 3/2003 | Datta et al. | |
| 6,544,544 | B2 | 4/2003 | Hunter | |
| 6,569,191 | B1 | 5/2003 | Hogan | |
| 6,569,195 | B2 | 5/2003 | Yang | |
| 6,585,764 | B2 | 7/2003 | Wright | |
| 6,589,546 | B2 | 7/2003 | Kamath | |
| 6,592,617 | B2 | 7/2003 | Thompson | |
| 6,599,928 | B2 | 7/2003 | Kunz | |
| 6,605,115 | B1 | 8/2003 | Cooke | |
| 6,632,242 | B2 | 10/2003 | Igaki | |
| 6,632,446 | B1 * | 10/2003 | Hubbell et al. | 424/423 |
| 6,645,518 | B2 | 11/2003 | Tedeschi | |
| 6,656,506 | B1 * | 12/2003 | Wu et al. | 424/489 |
| 6,656,966 | B2 | 12/2003 | Garvy | |
| 6,663,881 | B2 | 12/2003 | Kunz | |
| 6,706,274 | B2 | 3/2004 | Herman | |
| 6,719,934 | B2 | 4/2004 | Stinson | |
| 6,730,064 | B2 | 5/2004 | Ragheb | |
| 6,737,447 | B1 | 5/2004 | Smith | |
| 6,743,462 | B1 | 6/2004 | Pacetti | |
| 6,753,454 | B1 | 6/2004 | Smith | |
| 6,776,796 | B2 | 8/2004 | Falotico | |
| 6,783,543 | B2 * | 8/2004 | Jang | 623/1.15 |
| 6,790,228 | B2 | 9/2004 | Hossainy | |
| 6,805,898 | B1 | 10/2004 | Wu et al. | |
| 6,808,536 | B2 | 10/2004 | Wright | |
| 6,855,366 | B2 | 2/2005 | Smith | |
| 6,869,973 | B2 | 3/2005 | Garvy | |
| 6,875,840 | B2 | 4/2005 | Stamler | |
| 6,884,429 | B2 | 4/2005 | Koziak | |
| 6,887,266 | B2 | 5/2005 | Williams et al. | |
| 6,887,485 | B2 | 5/2005 | Fitzhugh | |
| 6,908,622 | B2 | 6/2005 | Barry | |
| 6,932,930 | B2 | 8/2005 | DeSimone et al. | |
| 6,949,112 | B1 | 9/2005 | Sridharan et al. | |
| 6,974,475 | B1 | 12/2005 | Wall | |
| 6,991,647 | B2 | 1/2006 | Jadhav | |
| 6,997,948 | B2 | 2/2006 | Stinson | |
| 7,005,137 | B1 | 2/2006 | Hossainy et al. | |
| 7,008,397 | B2 | 3/2006 | Tweden | |
| 7,011,678 | B2 | 3/2006 | Tenerz | |
| 7,029,495 | B2 | 4/2006 | Stinson | |
| 7,063,884 | B2 | 6/2006 | Hossainy et al. | |
| 7,070,615 | B1 | 7/2006 | Igaki | |
| 7,087,709 | B2 | 8/2006 | Stamler | |
| 7,101,566 | B2 * | 9/2006 | Rosenblatt et al. | 424/423 |
| 7,141,061 | B2 | 11/2006 | Williams et al. | |
| 7,160,323 | B2 | 1/2007 | Pulnev et al. | |
| 7,160,592 | B2 * | 1/2007 | Rypacek et al. | 428/36.9 |
| 7,163,554 | B2 | 1/2007 | Williams et al. | |
| 7,163,562 | B2 | 1/2007 | Datta et al. | |
| 7,166,133 | B2 * | 1/2007 | Evans et al. | 623/23.51 |
| 7,217,286 | B2 | 5/2007 | Falotico | |
| 7,220,816 | B2 | 5/2007 | Pacetti et al. | |
| 7,223,286 | B2 | 5/2007 | Wright | |

| | | | | | | |
|---|---|---|---|---|---|---|
| 7,229,473 | B2 | 6/2007 | Falotico | 2005/0142315 A1 | 6/2005 | DeSimone et al. | |
| 7,252,679 | B2 | 8/2007 | Fischell et al. | 2005/0214343 A1 | 9/2005 | Tremble | |
| 7,279,005 | B2 | 10/2007 | Stinson | 2005/0214344 A1 | 9/2005 | Barrows et al. | |
| 7,279,175 | B2 | 10/2007 | Chen | 2006/0002977 A1 | 1/2006 | Dugan | |
| 7,285,287 | B2 | 10/2007 | Williams et al. | 2006/0009839 A1* | 1/2006 | Tan | 623/1.38 |
| 7,291,165 | B2 | 11/2007 | Rosenthal | 2006/0095123 A1* | 5/2006 | Flanagan | 623/1.46 |
| 7,292,885 | B2 | 11/2007 | Scott | 2006/0100568 A1 | 5/2006 | Tan | |
| 7,300,662 | B2 | 11/2007 | Falotico | 2006/0121087 A1 | 6/2006 | Williams et al. | |
| 7,318,945 | B2 | 1/2008 | Thornton | 2006/0142853 A1* | 6/2006 | Wang et al. | 623/1.46 |
| 7,348,319 | B2 | 3/2008 | Hirable | 2006/0147492 A1 | 7/2006 | Hunter et al. | |
| 7,348,364 | B2 | 3/2008 | Shalaby | 2006/0195059 A1 | 8/2006 | Freyman et al. | |
| 7,361,726 | B2 | 4/2008 | Pacetti et al. | 2006/0204738 A1 | 9/2006 | Dubrow et al. | |
| 7,378,106 | B2 | 5/2008 | Hossainy | 2006/0246108 A1 | 11/2006 | Pacetti et al. | |
| 7,387,641 | B2 | 6/2008 | Schmitt | 2006/0246208 A1* | 11/2006 | Mansouri et al. | 427/2.1 |
| 7,390,333 | B2 | 6/2008 | Dutta | 2007/0026132 A1 | 2/2007 | Williams et al. | |
| 7,416,559 | B2 | 8/2008 | Shalaby | 2007/0038284 A1 | 2/2007 | Williams et al. | |
| 7,419,502 | B2 | 9/2008 | Pulnev et al. | 2007/0093889 A1 | 4/2007 | Wu et al. | |
| 7,419,503 | B2 | 9/2008 | Pulnev et al. | 2007/0110787 A1 | 5/2007 | Hossainy et al. | |
| 7,419,504 | B2 | 9/2008 | Hossainy | 2007/0123539 A1 | 5/2007 | Wu | |
| 7,425,218 | B2 | 9/2008 | Keffler | 2007/0255422 A1 | 11/2007 | Wei et al. | |
| 7,438,712 | B2 | 10/2008 | Chouinard | 2007/0271763 A1 | 11/2007 | Huang et al. | |
| 7,445,628 | B2 | 11/2008 | Ragheb | 2007/0280851 A1 | 12/2007 | Freeman et al. | |
| 7,470,283 | B2 | 12/2008 | Dutta et al. | 2007/0281250 A1 | 12/2007 | Aono | |
| 7,488,444 | B2* | 2/2009 | Furst et al. ............... 420/429 | 2007/0282247 A1 | 12/2007 | Desai et al. | |
| 7,491,233 | B1 | 2/2009 | Ding | 2007/0283552 A1 | 12/2007 | Gale et al. | |
| 7,491,234 | B2* | 2/2009 | Palasis et al. ............ 623/1.42 | 2007/0293932 A1* | 12/2007 | Zilla et al. | 623/1.11 |
| 7,498,385 | B2* | 3/2009 | Swetlin et al. ............ 525/172 | 2007/0299504 A1 | 12/2007 | Gale et al. | |
| 7,504,125 | B1 | 3/2009 | Pacetti et al. | 2008/0008739 A1 | 1/2008 | Hossainy et al. | |
| 7,517,338 | B2 | 4/2009 | Freyman et al. | 2008/0091262 A1 | 4/2008 | Gale et al. | |
| RE40,816 | E | 6/2009 | Taylor | 2008/0145393 A1 | 6/2008 | Trollsas et al. | |
| 7,556,842 | B2 | 7/2009 | Worsham et al. | 2008/0147161 A1 | 6/2008 | Chen et al. | |
| 7,563,483 | B2 | 7/2009 | Hossainy et al. | 2008/0147164 A1 | 6/2008 | Gale et al. | |
| 7,585,516 | B2 | 9/2009 | Pacetti | 2008/0177375 A1 | 7/2008 | Chen et al. | |
| 7,594,928 | B2 | 9/2009 | Headley, Jr. et al. | 2008/0208316 A1* | 8/2008 | Shalev et al. | 623/1.15 |
| 7,604,699 | B2 | 10/2009 | Chen et al. | 2008/0275539 A1 | 11/2008 | Williams et al. | |
| 7,611,533 | B2 | 11/2009 | Bates et al. | 2008/0300669 A1 | 12/2008 | Hossainy | |
| 7,618,448 | B2 | 11/2009 | Schmitz | 2008/0306592 A1* | 12/2008 | Wang | 623/11.11 |
| 7,648,725 | B2 | 1/2010 | Van Sciver et al. | 2009/0005860 A1 | 1/2009 | Gale et al. | |
| 7,658,880 | B2 | 2/2010 | Wu | 2009/0018643 A1* | 1/2009 | Hashi et al. | 623/1.15 |
| 7,682,647 | B2 | 3/2010 | Hossainy et al. | 2009/0062904 A1 | 3/2009 | Furst | |
| 7,682,648 | B1 | 3/2010 | Ding et al. | 2009/0098176 A1* | 4/2009 | Helmus et al. | 424/422 |
| 7,718,213 | B1 | 5/2010 | Scheer | 2009/0099600 A1* | 4/2009 | Moore et al. | 606/246 |
| 7,731,740 | B2 | 6/2010 | Lafont et al. | 2009/0124956 A1* | 5/2009 | Swetlin et al. | 604/8 |
| 7,736,386 | B2 | 6/2010 | Pulney et al. | 2009/0138076 A1 | 5/2009 | Palasis et al. | |
| 7,758,908 | B2 | 7/2010 | Pham et al. | 2009/0138077 A1* | 5/2009 | Weber et al. | 623/1.46 |
| 7,761,968 | B2 | 7/2010 | Huang et al. | 2009/0157166 A1* | 6/2009 | Singhal et al. | 623/1.15 |
| 7,763,068 | B2 | 7/2010 | Pulney et al. | 2009/0157173 A1* | 6/2009 | Bjork, Jr. | 623/1.46 |
| 7,763,308 | B2 | 7/2010 | Chen et al. | 2009/0192583 A1* | 7/2009 | Tedeschi et al. | 623/1.11 |
| 7,767,726 | B2 | 8/2010 | Sutermeister et al. | 2009/0216104 A1 | 8/2009 | DeSimone et al. | |
| 7,776,381 | B1 | 8/2010 | Tang et al. | 2009/0285974 A1 | 11/2009 | Kerrigan et al. | |
| 7,776,382 | B2 | 8/2010 | Chappa et al. | 2009/0286761 A1 | 11/2009 | Cheng et al. | |
| 7,794,495 | B2 | 9/2010 | Gale et al. | 2009/0304769 A1 | 12/2009 | Kunkel et al. | |
| 7,794,776 | B1 | 9/2010 | Limon et al. | 2009/0317559 A1* | 12/2009 | Heidenau et al. | 433/201.1 |
| 7,794,777 | B2 | 9/2010 | Kokish et al. | 2010/0063585 A1* | 3/2010 | Hoffmann et al. | 623/1.46 |
| 7,833,261 | B2 | 11/2010 | Chen et al. | 2010/0076544 A1* | 3/2010 | Hoffmann et al. | 623/1.15 |
| 7,857,844 | B2* | 12/2010 | Norton et al. ............ 623/1.53 | 2010/0198344 A1 | 8/2010 | Omura et al. | |
| 7,875,233 | B2 | 1/2011 | Huang et al. | 2010/0241229 A1* | 9/2010 | Baehre et al. | 623/16.11 |
| 7,875,283 | B2 | 1/2011 | Hossainy et al. | 2010/0247597 A1* | 9/2010 | Chen et al. | 424/423 |
| 7,879,953 | B2 | 2/2011 | Pacetti | 2010/0298952 A1* | 11/2010 | Busold et al. | 623/23.71 |
| 7,901,452 | B2 | 3/2011 | Gale et al. | 2011/0060403 A9* | 3/2011 | Nakatani et al. | 623/1.49 |
| 7,919,162 | B2 | 4/2011 | DeSimone et al. | 2011/0238162 A1* | 9/2011 | Busold et al. | 623/1.46 |
| 7,923,022 | B2 | 4/2011 | Wang et al. | 2011/0295288 A1* | 12/2011 | Khosrovaninejad | 606/153 |
| 7,951,185 | B1 | 5/2011 | Abbate et al. | 2011/0319987 A1* | 12/2011 | Palasis et al. | 623/1.46 |
| 7,971,333 | B2 | 7/2011 | Gale et al. | 2012/0038087 A1* | 2/2012 | Wang | 264/400 |
| 7,972,616 | B2 | 7/2011 | Dubrow et al. | 2012/0160408 A1* | 6/2012 | Clerc et al. | 156/280 |
| 7,985,441 | B1 | 7/2011 | Tang et al. | 2013/0158652 A1* | 6/2013 | Palasis et al. | 623/1.46 |
| 8,003,156 | B2 | 8/2011 | Van Sciver | | | | |
| 8,016,879 | B2 | 9/2011 | Gale et al. | | | | |
| 8,043,553 | B1 | 10/2011 | Durcan | | | | |
| 8,137,396 | B2* | 3/2012 | Busold et al. ............. 623/1.38 | | | | |
| 2002/0026231 | A1* | 2/2002 | Shannon et al. .......... 623/1.13 | | | | |
| 2003/0088307 | A1* | 5/2003 | Shulze et al. ............. 623/1.15 | | | | |
| 2004/0044405 | A1 | 3/2004 | Wolff | | | | |
| 2004/0068078 | A1 | 4/2004 | Milbocker | | | | |
| 2004/0106987 | A1 | 6/2004 | Palasis | | | | |
| 2004/0117008 | A1* | 6/2004 | Wnendt et al. ............ 623/1.46 | | | | |
| 2004/0181277 | A1 | 9/2004 | Furst | | | | |
| 2004/0260272 | A1 | 12/2004 | Friedman et al. | | | | |
| 2005/0113909 | A1* | 5/2005 | Shannon et al. .......... 623/1.46 | | | | |

FOREIGN PATENT DOCUMENTS

| | | |
|---|---|---|
| EP | 1382628 | 1/2004 |
| EP | 1400218 | 3/2004 |
| EP | 1700872 | 9/2006 |
| WO | WO 99/34750 | 7/1999 |
| WO | WO 2008/076383 | 6/2008 |
| WO | WO 2009/158290 | 12/2009 |

OTHER PUBLICATIONS

International Search Report dated Jul. 21, 2010 for International Patent Application No. PCT/US2010/035417 (2pgs.).

Examination Report dated Jan. 21, 2011, issued in GB Application No. GB1008366.5.
Search and Examination Report dated Sep. 1, 2010 issued in GB Application No. GB1008366.5.

Examination Report dated May 5, 2011, issued in GB Application No. GB1008366.5.

* cited by examiner

MEDICAL IMPLANT

This application is a continuation of, and claims priority to, U.S. patent application Ser. No. 13/183,104, which is in turn a continuation-in-part of, and claims the benefit of priority to, U.S. patent application Ser. No. 12/783,261, filed May 19, 2010, by inventors Lee Core et al., entitled "Medical Implant," and further claims the benefit of priority to U.S. patent application Ser No. 61/179,834, filed May 20, 2009, by inventors Lee Core et al., entitled "Medical Implant," to U.S. patent application Ser. No. 61/227,308, filed Jul. 21, 2009, by inventors Lee Core et al., entitled "Medical Implant," and to U.S. patent application Ser. No. 61/251,984, filed Oct. 15, 2009, by inventors Lee Core et al. The entire disclosure of each of these applications is hereby incorporated by reference for all purposes.

FIELD OF THE INVENTION

The present invention relates to medical implants, and more specifically, to self-expanding medical implants that are intended for placement within a lumen or cavity of a patient.

BACKGROUND

A variety of medical conditions are treatable by the implantation of tubular devices into natural body lumens. For example, it is commonplace to implant metallic stents into the coronary arteries of patients with heart disease following balloon angioplasty to minimize the risk that the arteries will undergo restenosis. Recently, commercial stents have included drug-eluting polymer coatings that are designed to further decrease the risk of restenosis. Other examples of conventional tubular medical implants include woven grafts and stent-grafts that are used to span vascular aneurysms, polymeric tubes and catheters that are used to bypass strictures in the ureter and urethra, and stents that are used in the peripheral vasculature, prostate, and esophagus.

Despite the evolution of metallic stents, they continue to have limitations such as the possibility of causing thrombosis and vascular remodeling. While the use of biodegradable and biostable polymeric materials for stents and other implantable devices has been proposed to eliminate the possible long-term effects of permanent implants, the use of such materials has been hindered by relatively poor expandability and mechanical properties. For example, the expansion characteristics and radial strength of prototype stents made from biodegradable and biostable polymeric materials has been significantly lower than that of metallic stents. This is particularly the case where such stents are low profile and make use of small diameter fibers or thin walled struts that comprise the stent body. Furthermore, the degradation rate and the manner in which such devices degrade in the body has been difficult to control. Finally, where such devices are used as a drug delivery vehicle, the drug elution rate has been difficult to reproducibly characterize.

There is therefore a need for low-profile, self-expanding implantable tubular devices that have sufficient expansion characteristics, strength and other mechanical and drug release properties that are necessary to effectively treat the medical conditions for which they are used.

SUMMARY

In one aspect, the present invention includes an implantable medical device for placement within a lumen or cavity of a patient. In another aspect, the present invention includes a method of loading the medical device into a delivery catheter just prior to being implanted into a patient. In another aspect, the present invention includes a method of treating a patient by delivering the medical device to a target location within the patient. In yet another aspect, the present invention includes a kit that comprises the implantable medical device.

The implantable medical devices of the present invention are generally tubular, self-expanding devices. The devices have a combination of structure, composition, and/or strengthening means that provide them with exceptional expandability and mechanical properties when compared with conventional self-expanding devices.

In one embodiment, the implantable medical device comprises a self-expanding tubular structure that comprises at least one strand. The at least one strand comprises a first polymer characterized by a modulus of elasticity greater than about 1 GPa. The implantable medical device further includes a strengthening means comprising a second polymer at least partially coating the strand. The second polymer is characterized by a percent elongation to break that is greater than about 150 percent at body temperature (37° C.). The second polymer increases the mass of the self-expanding tubular structure by at least about 20 percent.

In another embodiment, the implantable medical device comprises a self-expanding tubular structure that comprises at least one strand comprising a first polymer. The implantable medical device further includes a strengthening means comprising a second polymer at least partially coating the strand. The second polymer comprises a first elastic component having a Tg less than about 37° C. and a second component that is harder than the first component. The second polymer increases the mass of the self-expanding tubular structure by at least about 20 percent.

In other embodiments, the implantable medical device comprises a self-expanding tubular structure comprising a unitary framework rather than at least one strand. In certain embodiments, the implantable medical device comprises a therapeutic agent for delivery into a patient's body.

DESCRIPTION OF PREFERRED EMBODIMENTS

The present invention provides for self-expanding medical implants that have expansion characteristics and mechanical properties that render them suitable for a broad range of applications involving placement within bodily lumens or cavities. As used herein, "device" and "implant" are used synonymously. Also as used herein, "self-expanding" is intended to include devices that are crimped to a reduced configuration for delivery into a bodily lumen or cavity, and thereafter tend to expand to a larger suitable configuration once released from the delivery configuration, either without the aid of any additional expansion devices or with the partial aid of balloon-assisted or similarly-assisted expansion. When compared with conventional self-expanding medical implants, the implants of the present invention recover to an exceptionally high percentage of their manufactured diameter after being crimped and held in a small diameter for delivery into a bodily lumen. Moreover, when compared with conventional self-expanding implants and particularly polymeric implants, the implants of the present invention are characterized by much improved strength and other desired mechanical properties. As used herein, "strength" and "stiffness" are used synonymously to mean the resistance of the medical implants of the present invention to deformation by radial forces. Examples of strength and stiffness measurements, as used to characterize the medical implants of the present invention, include radial resistive force and chronic outward force, as further defined herein.

Figure 1:
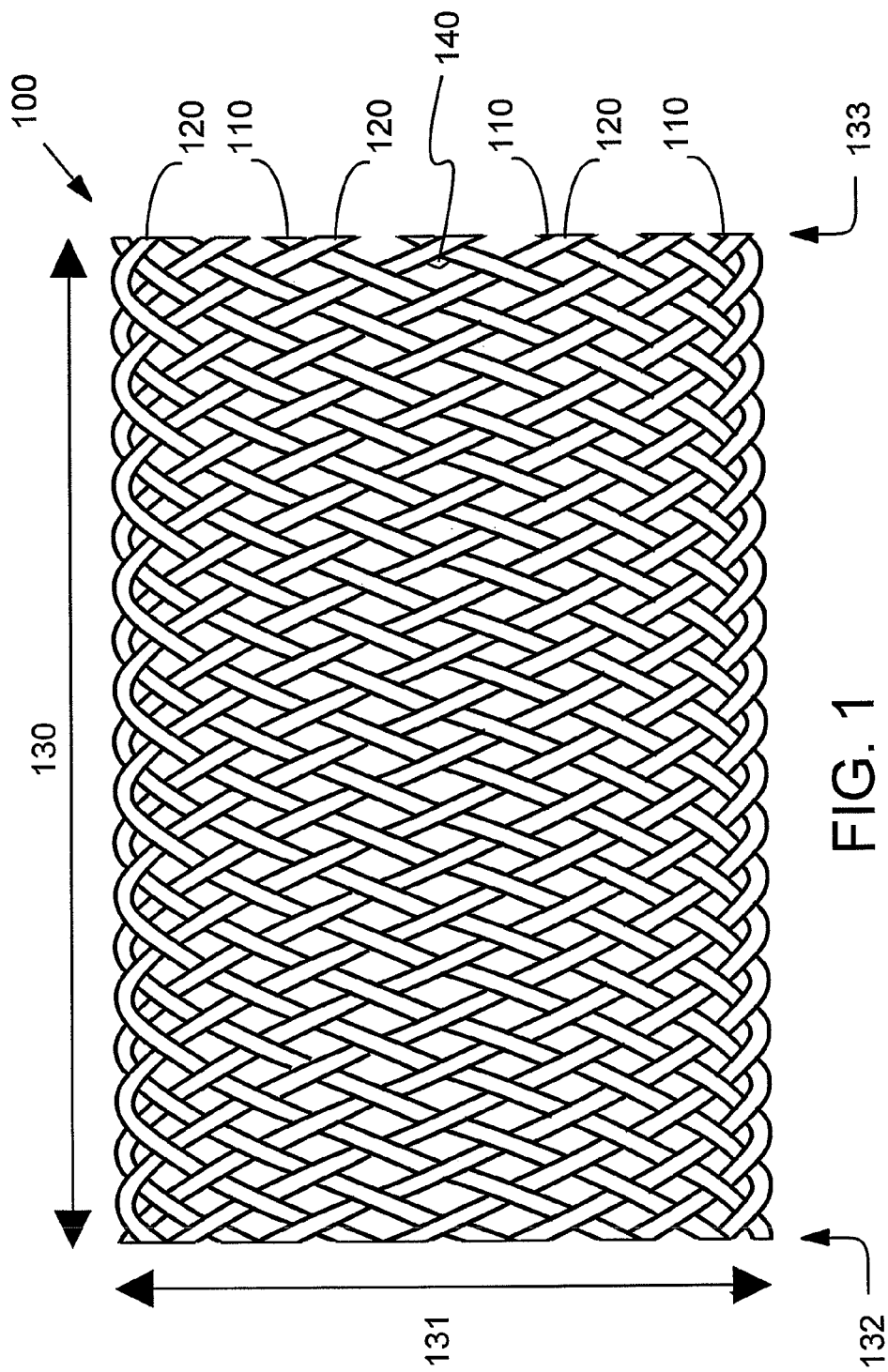
FIG. 1 is a side view of an implantable braided medical device, in accordance with an embodiment of the present invention.

In one embodiment shown in FIG. 1, the implant 100 preferably comprises at least one strand woven together to form a substantially tubular configuration having a longitudinal dimension 130, a radial dimension 131, and first and second ends 132, 133 along the longitudinal dimension. As used herein, "woven" is used synonymously with "braided." For example, the tubular configuration may be woven to form a tubular structure comprising two sets of strands 110 and 120, with each set extending in an opposed helix configuration along the longitudinal dimension of the implant. The sets of strands 110 and 120 cross each other at a braid angle 140, that may be constant or may change along the longitudinal dimension of the implant. Preferably, there are between about 16 and about 96 strands used in the implants of the present invention, and the braid angle 140 is within the range of about 90 degrees to about 135 degrees throughout the implant. The strands are woven together using methods known in the art, using known weave patterns such as Regular pattern "1 wire, 2-over/2-under", Diamond half load pattern "1 wire, 1-over/1-under", or Diamond pattern "2 wire, 1-over/1-under".

Although the strands may be made from biostable polymeric or metallic materials, they are preferably made from at least one biodegradable polymer that is preferably fully absorbed within about two years of placement within a patient, and more preferably within about one year of placement within a patient. In some embodiments, the strands are fully absorbed within about six or fewer months of placement within a patient. The first and second strand sets 110, 120 may be made from the same or different biodegradable polymer. Non-limiting examples of biodegradable polymers that are useful in the at least one strand of the present invention include poly lactic acid (PLA), poly glycolic acid (PGA), poly trimethylene carbonate (PTMC), poly caprolactone (PCL), poly dioxanone (PDO), and copolymers thereof. Preferred polymers are poly(lactic acid co-glycolic acid) (PLGA) having a weight percentage of up to about 20% lactic acid, or greater than about 75% lactic acid (preferably PLGA 85:15), with the former being stronger but degrading in the body faster. The composition of PLGA polymers within these ranges may be optimized to meet the mechanical property and degradation requirements of the specific application for which the implant is used. For desired expansion and mechanical property characteristics, the materials used for the strands preferably have an elastic modulus within the range of about 1 to about 10 GPa, and more preferably within the range of about 6-10 GPa.

To facilitate the low-profile aspects of the present invention (e.g., the delivery of the implants into small diameter bodily lumens or cavities), the strands used in the implant 100 preferably have a diameter in the range of from about 125 microns to about 225 microns, and are more preferably less than about 150 microns in diameter. The use of small diameter strands results in an implant with minimal wall thickness and the preferred ability to collapse (i.e., to be crimped) within low diameter catheter delivery systems. Where multiple strands are used, they may be of substantially equal diameters within this range, or first strand set 110 may be of a different general diameter than second strand set 120. In either event, the diameters of strands are chosen so as to render the implant 100 preferably deliverable from a 10 French delivery catheter (i.e., 3.3 mm diameter) or smaller, and more preferably from a 7 French delivery catheter (i.e., 2.3 mm diameter) or smaller. The ability to place the implant of the present invention into small diameter delivery catheters allows for its implantation into small diameter bodily lumens and cavities, such as those found in the vascular, biliary, uro-genital, iliac, and tracheal-bronchial anatomy. Exemplary vascular applications include coronary as well as peripheral vascular placement, such as in the superficial femoral artery (SFA). It should be appreciated, however, that the implants of the present invention are equally applicable to implantation into larger bodily lumens, such as those found in the gastrointestinal tract.

Figure 2:
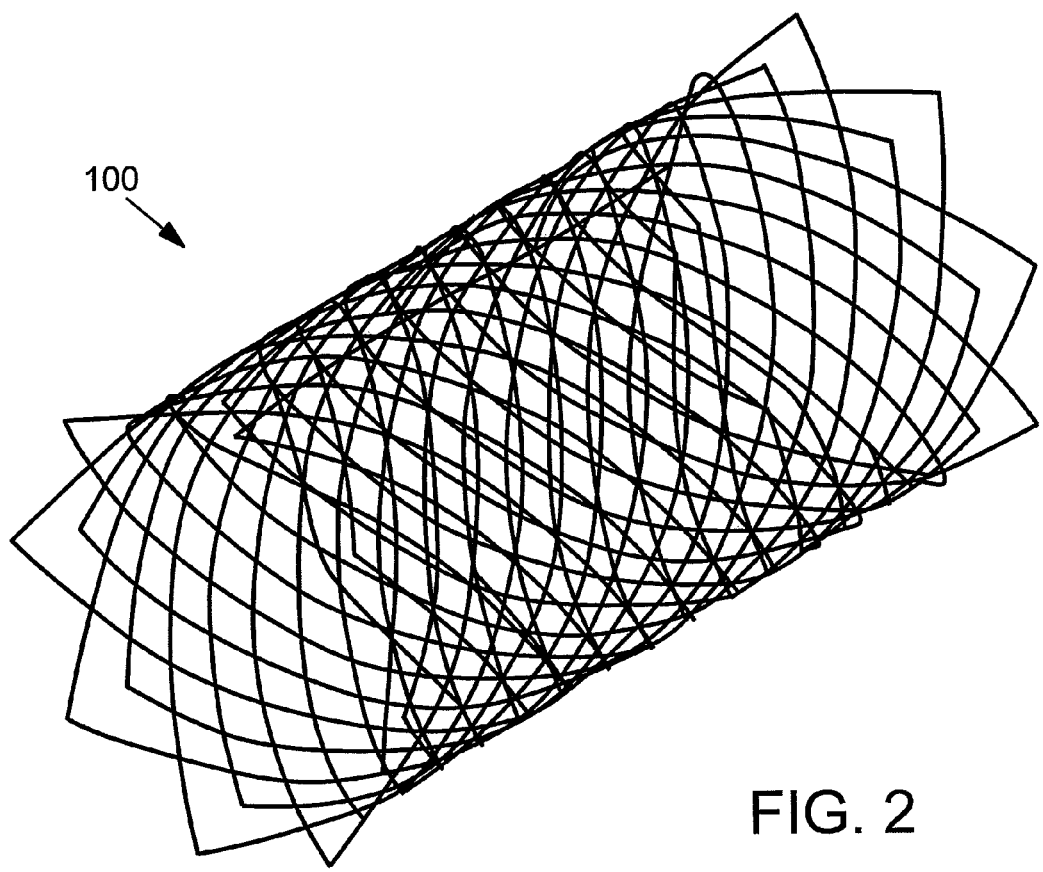
FIG. 2 is a side view of an implantable unitary framework medical device, in accordance with an embodiment of the present invention.

In another embodiment of the present invention, the implant is a non-woven, self-expanding structure, such as a unitary polymeric framework. As shown in FIG. 2, the non-woven implant 100 is preferably characterized by a regular, repeating pattern such as a lattice structure. The use of a unitary framework may provide a reduced profile when compared to the use of woven strands, which yield a minimum profile that is the sum of the widths of overlapping strands. In addition, a unitary framework eliminates the possible change in length of the implant associated with crimping and subsequent expansion, known as foreshortening, which is common in braided stents. When the implant 100 is a unitary framework, it is fabricated using any suitable technique, such as by laser cutting a pattern into a solid polymer tube. In a preferred embodiment, when the implant 100 is a unitary framework, it is formed by laser cutting and includes a wall thickness of between about 75 and about 100 microns. It should be recognized that while the present invention is described primarily with reference to woven strand configurations, aspects of the present invention are equally applicable to non-woven, self-expanding structures unless necessarily or expressly limited to woven configurations.

There are a variety of strengthening means that are useful in the present invention to help provide the expansion and mechanical properties that are needed to render the implant 100 effective for its intended purpose. Two measures of such mechanical properties that are used herein are "radial resistive force" ("RRF") and "chronic outward force" ("COF"). RRF is the force that the implant applies in reaction to a crimping force, and COF is the force that the implant applies against a static abutting surface. Without wishing to be bound by theory, the inventors believe that the self-expanding implants of the present invention should preferably recover to a high percentage of their as-manufactured configuration after being crimped for insertion into the body, and the thus expanded implant should have a relatively high RRF to be able to hold open bodily lumens and the like, yet have a relatively low COF so as to avoid applying possibly injurious forces against the walls of bodily lumens or the like. For example, the implants of the present invention preferably expand to at least 90% of their as manufactured configuration after being crimped, have an RRF of at least about 200 mm Hg, have an acute COF (at the time of delivery into a bodily lumen or cavity) of about 40-200 mm Hg, and a COF of less than about 10 mm Hg after about 28 days in vivo.

Figure 3:
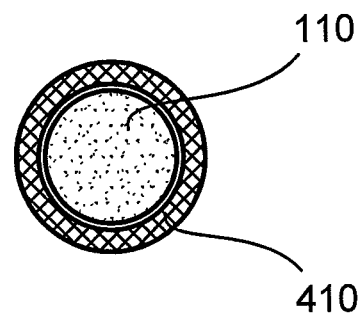
FIG. 3 is a cross-sectional view of a strand of an implantable medical device in accordance with an embodiment of the present invention that includes a support coating.

In one embodiment, the strengthening means is a support coating 410 on at least one of the strands of the implant 100. Although referred to herein as a "coating," the support coating 410 does not necessarily coat the entire implant 100, and may not form a discrete layer over the stands or unitary framework of the implant 100; rather, the support coating 410 and underlying strands or unitary framework may be considered as a composite structure. The support coating 410 is made from an elastomeric polymer that, due to its elastic nature when compressed or elongated, applies a force to implant 100 that acts in favor of radial expansion and axial contraction, thus enhancing radial strength. The polymer of the support coating 410 is preferably biodegradable. Alternatively, the support coating 410 is made from a shape memory polymer or a polymer that otherwise contracts upon heating to body temperature. The inventors have surprisingly found that the use of support coatings on the polymeric implants of the present invention can result in the recovery of more than 90% of implant diameter post-crimping, and yield significantly higher radial forces when compared with uncoated implants or even with self-expanding metallic stents. The support coating 410 may be applied as a conformal coating (as shown in cross-section of an individual strand in FIG. 3), may be partially applied to one or more individual strands such that the support coating 410 is applied to only a portion of the implant along its longitudinal dimension, or may be applied to only the inner or outer diameter of one or more individual strands. Also, the support coating 410 may optionally vary in weight along the length of the implant; for example, the ends of the implant may be coated with a thicker layer than the mid-section to provide added support to the ends of the implant. In addition, the support coating may accumulate at the crossover points or "nodes" of the woven device, which has the effect of aiding in diameter recovery and the achievement of preferred COF and RRF values.

Examples of polymer materials used for the support coating 410 include suitable thermoplastic or thermoset elastomeric materials that yield the elongation, mechanical strength and low permanent deformation properties when combined with the implant strand(s). The inventors have found examples of suitable polymers to include certain random copolymers such as poly(lactic acid-co-caprolactone) (PLCL), poly(glycolide-co-caprolactone) (PGCL), and poly (lactic acid-co-dioxanone) (PLDO), certain homopolymers such as poly trimethylene carbonate (PTMC), and copolymers and terpolymers thereof. Such polymers are optionally crosslinked with a crosslinker that is bi- or multi-functional, polymeric, or small molecule to yield a thermoset polymer having a glass transition temperature (Tg) that is preferably lower than body temperature (37° C.), more preferably lower than room temperature (25° C.), and most preferably lower than about 5° C. The thermoset elastomers provide a high elongation to break with low permanent deformation under cyclic mechanical testing.

In one preferred embodiment, the polymer material used for the support coating 410 is a biodegradable thermoset elastomer synthesized from a four arm PGCL polymer having a weight ratio of approximately 50:50 GA:CL that is crosslinked with hexamethylene diisocyanate (HDI) to give a polyester with urethane crosslinks. Without wishing to be bound by theory, the inventors believe that the combination of the elastic segment (polyester portion) and the interactions (such as hydrogen bonding, allophanate or biuret formation) between the urethane segments of such polymers, in addition to a certain crosslinking density, yields preferred properties such as a high degree of elastic recovery under cyclic mechanical strain and high overall elasticity.

In other preferred embodiments, the support coating comprises PLCL having a weight ratio of approximately 50:50 PL:CL. In yet another preferred embodiment, a PLCL 50:50 crosslinked with hexamethylene diisocyanate support coating is applied to a PLGA 75:25 braided implant.

The polymer material used for support coating 410 may be optimized for desired mechanical properties. For example, the inventors have found that the molecular weight of such polymers may be manipulated to enhance coating performance. As an example, when PLCL 50:50 crosslinked with hexamethylene diisocyanate is used as the support coating of the present invention, the inventors have found that a molecular weight (Mn) between about 30 kDa and 100 kDa, preferably from 33 k to 65 k, results in a lower modulus of elasticity and a higher strain to fracture, thus making the coating better able to adhere to a PLGA braided implant during crimping and post-crimping expansion and therefore less likely to fracture during deployment. Similarly, the inventors have found that when PGCL 50:50 crosslinked with hexamethylene diisocyante is used as the support coating of the present invention, a molecular weight (Mn) from 8 kDa to 20 kDa does not yield an appreciable change in properties, but that a further increase in molecular weight to 50 kDa results in a four-fold increase in the strain at failure of the coating material. As such, a preferred range of molecular weight (Mn) for PGCL used in the implants of the present invention is about 23 kDa to about 50 kDa. Additionally, the inventors have found that the viscosity of the spray coating solution, the weight percent of crosslinker used in the spray coating solution, and the temperature and duration of the support coating crosslinking process can be optimized to provide preferred coating morphologies and radial forces.

The support coating 410 is coated onto the surface of the implant 100 using any suitable method, such as spraying, dipping, electrospraying, rolling, and the like. If implant 100 is a woven structure, the support coating 410 may be applied to individual strands prior to forming the woven structure, or to the woven structure after the formation thereof. In this case, owing to surface tension, the coating preferably collects at intersection points between strands. If implant 100 is a non-woven structure, the support coating 410 may be applied, for example, to a solid polymer tube either before or after the removal of material such as by laser cutting to form a patterned, non-woven structure.

The amount of support coating 410 applied to the implant 100 has been identified as one of the factors that contribute to the expansion characteristics and mechanical strength of the implant. Preferably, the application of the support coating 410 increases the weight of the uncoated implant 100 by about 20% to about 100%, more preferably, by about 24% to about 70%, and most preferably by about 30% to about 60%.

In another embodiment, the strengthening means includes the attachment of strand sets 110, 120 at one or more intersections of the strands along the longitudinal dimension of the implant 100. Such attachment may be achieved by use of an adhesive, or by fusing the strands at predetermined intersections such as by heat, laser, or ultrasound. In this embodiment, the strands comprise materials having sufficient elasticity such that the local strains induced by the adhesive/welded joints would not cause plastic deformation thereof.

In yet another embodiment, the strengthening means includes the incorporation of additives into one or more of the strands. In one example, such additives are neutralizing agents such as calcium salts (e.g., calcium carbonate or calcium phosphate) or other salts such as barium salts that increase the mechanical strength of the strands into which they are incorporated, and further act to neutralize any acidic byproducts resulting from the degradation of the strand material(s). In another example, such additives are plasticizers such as polyethylene glycol (PEG) that dissolve from the strand(s) in vivo, thus increasing the flexibility of the strand(s) and the implant over time.

Figure 4:
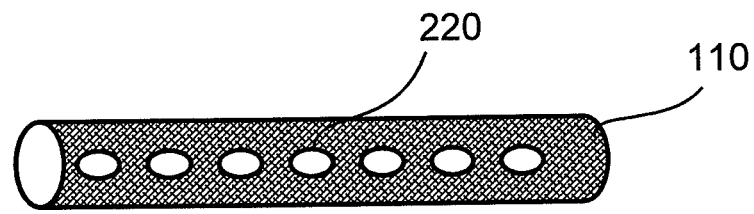
FIG. 4 is a side view of a strand of an implantable medical device in accordance with an embodiment of the present invention that includes discrete areas of therapeutic agent thereon.

In one embodiment, the implant 100 delivers one or more therapeutic agents at the site of implantation. The therapeutic agent(s) may be applied to one or more strands for delivery therefrom in a number of ways. In one example, the therapeutic agent(s) are embedded within a conformal polymer coating 210 that adheres to one or more individual strands of the implant 100. Such a coating 210 is preferably made from a biodegradable polymer admixed with the therapeutic agent(s) such that the agent is eluted from the polymer over time, or is released from the coating as it degrades in vivo. In another example as shown in FIG. 4, one or more therapeutic agents are applied in discrete areas 220 on one or more individual strands (shown as length of individual strand). Like coating 210, discrete areas 220 are preferably made from a biodegradable polymer admixed with the therapeutic agent(s) and eluted from the polymer over time, or are released from the coating as it degrades in vivo. In either of coating 210 or discrete areas 220, the biodegradable polymer may be the same as or different from the biodegradable polymer(s) used in the strands of the implant. In yet another example, the therapeutic agent(s) are admixed within the strand(s) of the implant 100 such that the agent(s) are eluted from the one or more strands over time, or are released from the one or more strands as the strand(s) degrade in vivo. In yet another example, the therapeutic agent(s) are admixed within a support coating, as described herein. Likewise, in embodiments in which the implant 100 is a non-woven structure, the therapeutic agent(s) may be admixed with the polymer used to fabricate the implant 100.

The therapeutic agent(s) used in the present invention are any suitable agents having desired biological effects. For example, where the implant of the present invention is used to combat restenosis, the therapeutic agent is selected from anti-thrombogenic agents such as heparin, heparin derivatives, urokinase, and PPack (dextrophenylalanine proline arginine chloromethylketone), enoxaparin, hirudin; anti-proliferative agents such as angiopeptin, or monoclonal antibodies capable of blocking smooth muscle cell proliferation, acetylsalicylic acid, paclitaxel, sirolimus, tacrolimus, everolimus, zotarolimus, vincristine, sprycel, amlodipine and doxazosin; anti-inflammatory agents such as glucocorticoids, betamethasone, dexamethasone, prednisolone, corticosterone, budesonide, estrogen, sulfasalazine, rosiglitazone, mycophenolic acid, and mesalamine; immunosuppressants such as sirolimus, tacrolimus, everolimus, zotarolimus, and dexamethasone; anti-neoplastic/antiproliferative/anti-mitotic agents such as paclitaxel, 5-fluorouracil, cisplatin, vinblastine, cladribine, vincristine, epothilones, methotrexate, azathioprine, halofuginone, adriamycin, actinomycin and mutamycin; endostatin, angiostatin and thymidine kinase inhibitors, and its analogs or derivatives; anesthetic agents such as lidocaine, bupivacaine, and ropivacaine; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, hirudin, prostaglandin inhibitors, platelet inhibitors and anti-platelet agents such as trapidil or liprostin, tick antiplatelet peptides; DNA demethylating drugs such as 5-azacytidine, which is also categorized as a RNA or DNA metabolite that inhibit cell growth and induce apoptosis in certain cancer cells; vascular cell growth promotors such as growth factors, Vascular Endothelial Growth Factors (VEGF, all types including VEGF-2), growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin; angiogenic substances, such as acidic and basic fibrobrast growth factors, estrogen including estradiol (E2), estriol (E3) and 17-Beta Estradiol; drugs for heart failure, such as digoxin, beta-blockers, angiotensin-converting enzyme (ACE) inhibitors including captopril and enalopril, statins and related compounds; and macrolides such as sirolimus and everolimus. Preferred therapeutic agents used in the present invention to treat restenosis and similar medical conditions include sirolimus, everolimus, zotarolimus, vincristine, sprycel, dexamethasone, and paclitaxel. Also preferred is the use of agents that have a primary mechanism of action of inhibiting extracellular matrix remodeling, and a secondary mechanism of action of inhibiting cell proliferation. Such agents include 5-fluorouracil, valsartan, doxycyclin, carvedilol, curcumin, and tranilast.

Figure 5:
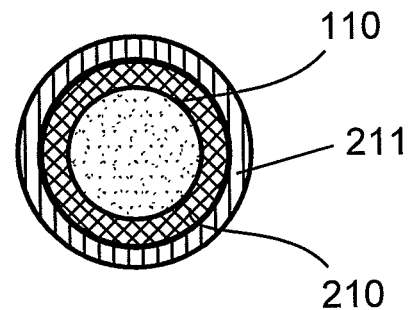
FIG. 5 is a cross-sectional view of a strand of an implantable medical device in accordance with an embodiment of the present invention that includes a therapeutic agent coating and a topcoat.

Coating 210 or areas 220 containing one or more therapeutic agents are applied to implant 100 by any suitable method, such as spraying, electrospraying, rolling, dipping, chemical vapor deposition, and potting. As an alternate embodiment, coating 210 or areas 220 is further coated with a biodegradable topcoat as shown in FIG. 5 (individual strand shown in cross-section), that acts to regulate the delivery of the therapeutic agent from coating 210 or areas 220 into bodily tissue. In one embodiment, the topcoat 211 acts as a diffusion barrier such that the rate of delivery of the therapeutic agent(s) are limited by the rate of its diffusion through the topcoat 211. In another embodiment, the therapeutic agent(s) cannot diffuse through the topcoat 211 such that delivery thereof is simply delayed until the degradation of the topcoat 211 is complete. The topcoat 211 preferably comprises a biodegradable polymer that is the same as or different from that of the coating 210 or the strands. If implant 100 is a woven structure, coatings 210, 220, or 211 may be applied to individual strands prior to forming into the woven structure, or to the woven structure after the formation thereof. If implant 100 is a non-woven structure, coatings 210, 220, or 211 may be applied, for example, to a solid polymer tube either before or after the removal of material such as by laser cutting to form a patterned, non-woven structure. In embodiments that include support coating 410, the coatings 210, 220, and/or 211 are preferably applied over such support coating 410, or the support coating 410 itself may include the therapeutic agent(s).

The implant 100 of the present invention is self-expanding in that it is manufactured at a first diameter, is subsequently reduced or "crimped" to a second, reduced diameter for placement within a delivery catheter, and self-expands towards the first diameter when extruded from the delivery catheter at an implantation site. The first diameter is preferably at least 20% larger than the diameter of the bodily lumen into which it is implanted. The implant 100 is preferably designed to recover at least about 80% and up to about 100% of its manufactured, first diameter. The inventors have found that implants in accordance with the present invention have a recovery diameter greater than 80%, and preferably greater than 90%, of the manufactured, first diameter after being crimped into exemplary delivery catheters of either 1.8 mm or 2.5 mm inner diameter and held for one hour at either room temperature (25° C.) or body temperature (37° C.). Such implants a braided structure comprising 32 strands ranging in size from 0.122 mm to 0.178 mm, braided with an inner diameter ranging from 5 to 6 mm. In a preferred embodiment, the implant 100 has a manufactured, first diameter (inner) of about 4.0 mm to about 10.0 mm.

Various factors contribute to the radial strength of implant 100. For woven implant structures, these factors include the diameter(s) of the strands, the braid angle 140, the strand material(s), the number of strands used, and the use of strengthening means. The inventors have found that it is preferred that the woven implants of the present invention have a braid angle 140 within a range of about 90° to 135°, more preferably within a range of about 110° to 135°, and most preferably within a range of about 115° to 130°. The inventors have confirmed through experimentation that braid angle may affect certain mechanical properties of the implants of the present invention. For example, the inventors have found that while a braid angle of 110° for 6 mm PGCL coated braided implants made from PLGA 10:90 copolymer strands yields post-crimp RRF and COF values at 4.5 mm of 370 mm and 147 mm Hg, respectively, the same coated implants having a 127° braid angle are characterized by post-crimp RRF and COF values at 4.5 mm of 900 mm and 170 mm Hg, respectively. RRF and COF values for 7 mm PGCL coated PLGA 10:90 copolymer implants having a 140° braid angle were not obtainable because the samples buckled in the test equipment, thus demonstrating that a high braid angle may result in the inability of the implant to uniformly collapse during crimping into a catheter. Braid angle was also found to have an effect upon the ability of the implants of the present invention to recover to their as-manufactured diameters. For example, 7 mm PGCL coated braided implants made from PLGA 10:90 copolymer and having braid angles of 133°, 127°, and 110° were found to recover to about 96%, 94%, and 91% of their as-manufactured configurations, respectively, after being held at 37° C. for one hour.

Figure 6:
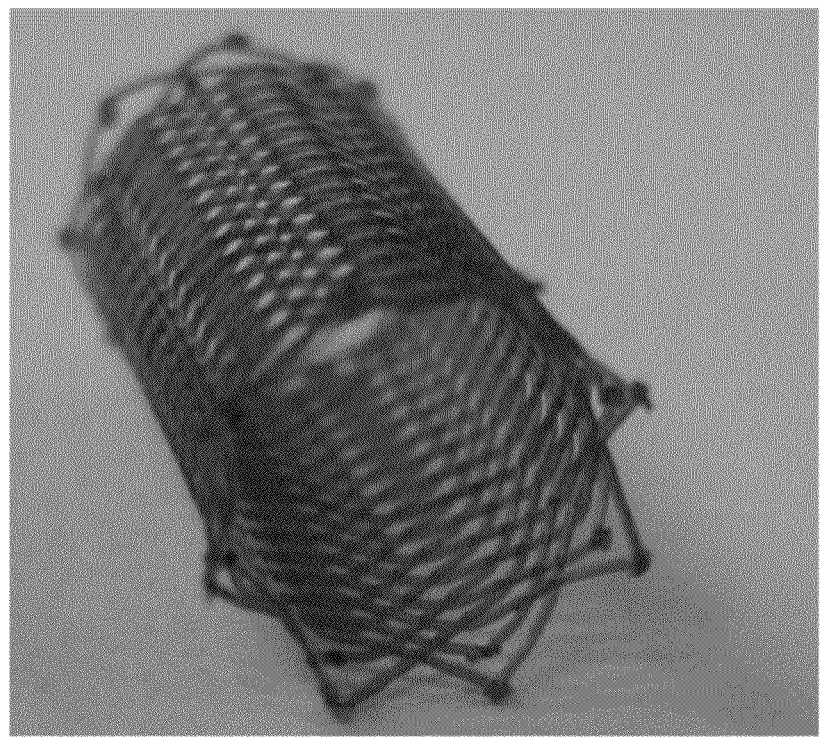
FIG. 6 is an end view of an implantable medical device in accordance with an embodiment of the present invention.

In another embodiment specific to woven structures, the ends of strands are fused in patterns on the outside and/or inside of the implant 100, as shown in FIG. 6. Fusing the strands in this manner causes the ends 132, 133 to flare outwards instead of curling inward, thus addressing a phenomenon in which the ends of the implant may naturally curl inward when the implant is crimped into a reduced configuration for insertion into a bodily lumen or cavity. In one embodiment, the ends are fused in patterns such that their final positions are axially staggered. Strands are fused, for example, by using heat, chemicals, adhesives, crimp swages, coatings (elastomeric or non-elastomeric), or other suitable fusing or joining techniques.

The implants of the present invention are preferably radiopaque such that they are visible using conventional fluoroscopic techniques. In one embodiment, radiopaque additives are included within the polymer material of one or more strands of implant 100. Examples of suitable radiopaque additives include particles comprising iodine, bromine, barium sulfate, and chelates of gadolinium or other paramagnetic metals such as iron, manganese, or tungsten. In another embodiment, the radiopaque groups, such as iodine, are introduced onto the polymer backbone. In yet another embodiment, one or more biostable or biodegradable radiopaque markers, preferably comprising platinum, iridium, tantalum, and/or palladium are produced in the form of a tube, coil, sphere, or disk, which is then slid over one or more strands of fiber to attach to the ends of implant 100 or at other predetermined locations thereon. When the marker is in the form of a tube or coil, it has a preferable wall thickness of about 0.050 to 0.075 mm and a length of about 0.3 to 1.3 mm. The tube is formed by extrusion or other methods known in the art. The coil is formed by winding a wire around a mandrel of desired diameter and setting the coil with heat or other methods known in the art.

To facilitate delivery, the implant 100 is preferably loaded into a delivery catheter just prior to being implanted into a patient. Loading the implant 100 in close temporal proximity to implantation avoids the possibility that the polymer of the implant 100 will relax during shipping, storage, and the like within the delivery catheter and therefore cannot fully expand to a working configuration. As such, one aspect of the invention includes a method of delivering an implant of the invention that comprises the step of loading the implant into a delivery catheter within a short period of time, and preferably within one hour, before implantation into a body lumen. It should be noted, however, that it is not required that the implants of the present invention are loaded into delivery catheters just prior to being implanted. In fact, one advantage of the present invention is that it provides self-expanding implantable medical devices with preferred expansion characteristics and mechanical properties even after being loaded in a delivery catheter for prolonged periods.

The present invention is further described with reference to the following non-limiting examples.

Example 1

Braided implants were manufactured using a PLGA 10:90 copolymer by spooling fiber spun monofilaments onto individual bobbins. Each bobbin was placed on a braiding machine, strung through rollers and eyelets and wrapped around a mandrel. The braiding tension of the machine was set for the size of the monofilament (i.e., 70 g min, 215 g max for 0.005" fiber). The pix/inch was set to obtain an ideal angle to maximize radial strength but still allow the braid to be removed from the mandrel (i.e., 110 to 135 degrees for a 6 mm mandrel). The braid pattern was selected and the monofilaments were braided off the spool onto the mandrel by the braiding machine. Tiewraps were used on the end of each mandrel to keep the tension on the filaments, which can be important for heat annealing and obtaining high modulus properties. The braided polymer was heat annealed on the mandrel, and then cut into desired lengths with a blade and removed from the mandrel. A representative implant was measured to have an outer diameter of about 6.0 mm and a length of about 20 mm.

Implants were coated with a support coating made from poly(glycolide-co-caprolactone) (PGCL) cured with hexamethylene diisocyanate. The PGCL 50:50 copolymer was prepared as follows. A 100 mL round-bottom flask was dried in oven at 110° C. and then cooled to room temperature under a nitrogen atmosphere. The flask was charged with $Sn(Oct)_2$ (15 mg), pentaerythritol (68 mg), glycolide (10.0 g), and ε-caprolactone (10.0 g), respectively. Subsequently, the flask was equipped with a magnetic stir bar and a three-way valve connected to a nitrogen balloon. The flask was thoroughly degassed under reduced pressure and flushed with nitrogen. The flask was then placed into an oil bath which was preheated to 170° C. The reaction was stirred at 170° C. for 24 h under a nitrogen atmosphere. After cooling to room temperature, the solid obtained was dissolved in dichloromethane and precipitated from anhydrous diethyl ether. The solution was decanted and the residual sticky solid was washed thoroughly with diethyl ether and dried in vacuum. Typically, around 18 g of polymer was recovered through the purification. GPC characterization revealed a number average molecular weight (Mn) of 39,900 and a polydispersity index (PDI) of 1.23.

The four-arm PGCL 50:50 (1.0 g) and HDI (375 μL) were dissolved in 20 mL dichloromethane to make a stock solution for spray-coating. A steel mandrel of 2 mm in diameter was mounted vertically onto a mechanical stirrer, and the braided implant was placed over the mandrel. A spray gun (Badger 150) was arranged perpendicular to the mandrel, and connected to a nitrogen cylinder and a reservoir containing the stock solution. The mechanical stirrer was turned on to spin the mandrel and the solution was sprayed onto the braid by applying the nitrogen flow. The coating weight could be controlled by the spray time. After spray coating, devices were dried in air for 1 h and then cured at 100° C. for 16 h. A catalyst such as tin octanoate or zinc octanoate may also be used in the curing process to reduce the curing time and/or temperature.

Coated devices were placed in an MSI radial force tester to obtain RRF and COF values, both measured in mm Hg, at time points prior to and subsequent to crimping the device to 2.5 mm.

Figure 7:
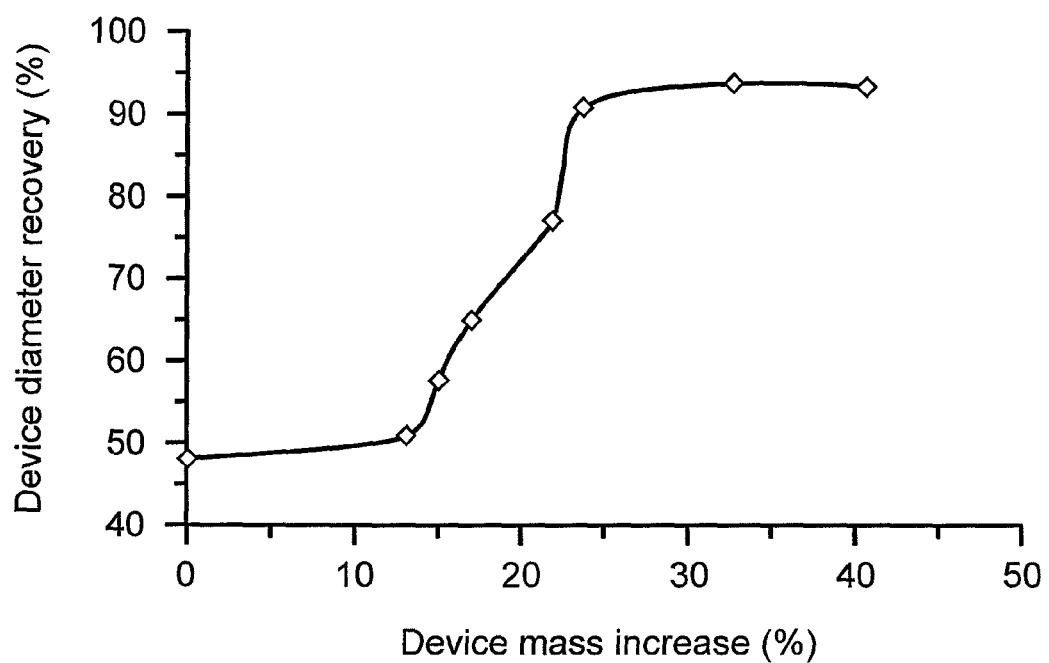
FIG. 7 is a graph of diameter recovery as a function of support coating weight, for certain embodiments of the present invention.

The inventors surprisingly found that whereas uncoated implants were able to recover to only about 50% of their original diameter after being crimped at 37° C. for one hour, the application of the PGCL/HDI coating resulted in a recovery of up to about 95% of the device original diameter. This effect was found to be at least partially dependent upon the coating weight on the implant. As illustrated in FIG. 7, diameter recovery was found to be related to the mass increase attributable to the application of the coating (i.e., coating weight), with an appreciable increase in the diameter recovery ability beginning when the increase in implant mass due to the application of the coating is about 15%. The effect of coating weight levels off when the increase in implant mass due to the application of the coating is at least about 20%, at which point the device recovery diameter is at least about 90%.

Figure 8:
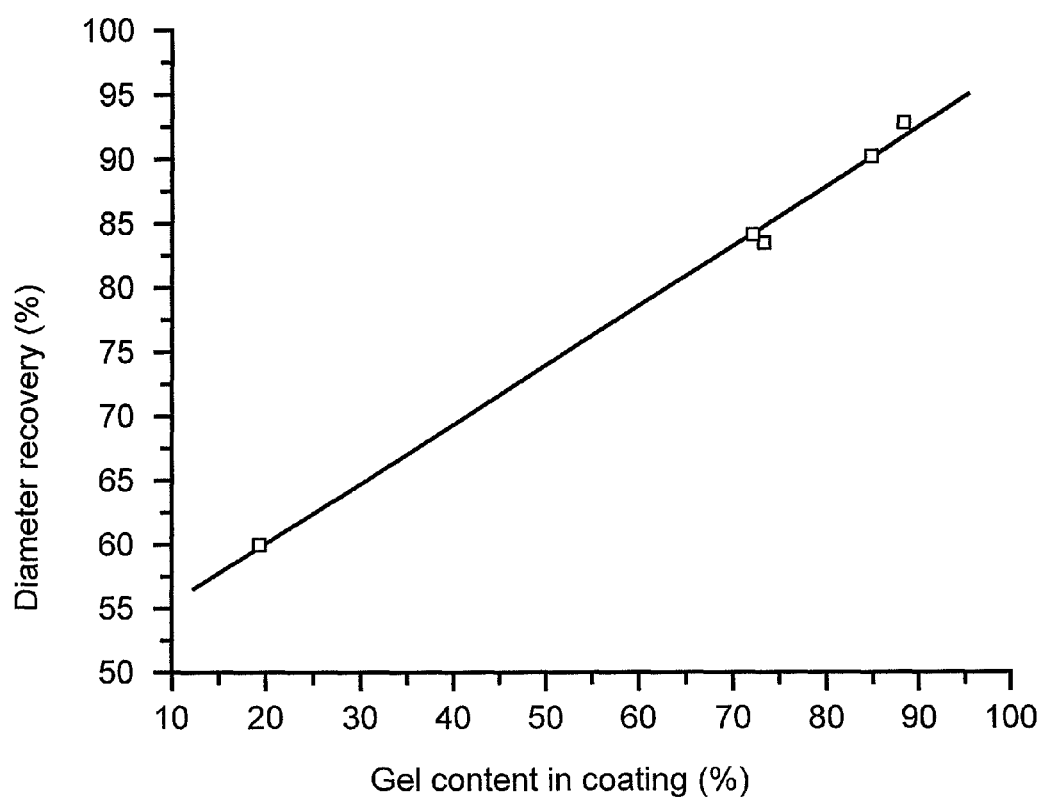
FIG. 8 is a graph of diameter recovery as a function of gel content within a support coating, for certain embodiments of the present invention.

Implant diameter recovery was also affected by the percent gel content in the coating, as shown in FIG. 8. Gel content is defined as the quantity of coating that is sufficiently crosslinked so that it is no longer soluble in a solvent. The calculation of gel content in the PGCL/HDI coating is described in Example 3. The inventors have found in this Example that a coating gel content of greater than about 80% is preferred to achieve a diameter recovery of at least about 90%.

Table I shows the percent recovery, radial resistive force (RRF) at a post-crimp diameter of 4.5 mm, and chronic outward force (COF) at a post-crimp diameter of 4.5 mm, for coated implants with varying coating weight. As can be seen from the data in Table I, the support coating increased the post-crimp recovery ability, RRF, and COF of the implants. Moreover, in addition to increasing recoverability of the implant acutely (i.e., after being crimped one hour in a 37° C. water bath), the support coating is able to increase recoverability chronically (i.e., after being crimped for five days at room temperature in air).

TABLE I

Percent recovery, RRF, and COF for coated implant samples that were crimped to 2.5 mm and held in water bath at 37° C.

| Sample No. | Sample Description | Water Bath Treatment | % Recovery after 2.5 mm Crimp | RRF at 4.5 mm (mmHg) | COF at 4.5 mm (mmHg) |
|---|---|---|---|---|---|
| 1 | 10:90 PLGA uncoated | 1 hour | 48 | 83.4 | 11.6 |
| 2 | 10:90 PLGA coated 45% | 1 hour | 93.5 | — | — |
| 3 | 10:90 PLGA coated 41% | 1 hour | 94.5 | 645.0 | 245.0 |
| 4 | 10:90 PLGA coated 33% | 1 hour | 94.6 | — | — |
| 5 | 10:90 PLGA coated 33% | 5 days at room T in air (no water bath) | 94.4 | — | — |
| 6 | 10:90 PLGA coated 24% | 1 hour | 91.5 | 1030.0 | 188.0 |
| 7 | 10:90 PLGA coated 22% | 1 hour | 77.9 | 897.0 | 84.0 |
| 8 | 10:90 PLGA coated 17% | 1 hour | 65.6 | 559.0 | 24.4 |
| 9 | 10:90 PLGA coated 15% | 1 hour | 58.2 | — | — |
| 10 | 10:90 PLGA coated 13% | 1 hour | 51.4 | 393.0 | −2.6 |
| 11 | PDO uncoated | 1 hour | 79.0 | 53.4 | 0 |
| 12 | PDO coated 37% | 1 hour | 83.6 | 863.0 | 115.0 |

The percent increase in implant weight due to the coating is shown in the Sample Description column.

Example 2

Implants and coating solutions were manufactured as described in Example 1. Instead of being applied uniformly to the implants, support coatings were applied to just the ends of the implants (i.e., approximately 4-5 mm at each end). Whereas the uncoated implant was able to recover only about 48% of its original diameter after being crimped to 2.5 mm and held in a water bath for one hour at 37° C., the implant coated at its ends was able to recover, under the same conditions, to about 82% of its original diameter. Moreover, for these same implants, the RRF and COF was increased from 83.4 mmHg and 11.6 mmHg to 595.0 mmHg and 55.0 mmHg, respectively.

Example 3

The gel content of a coated implant (such as the implant described in Example 1) was measured via extraction. The PGCL/HDI coated device was placed in 5 mL of dichloromethane and shaken at room temperature for about 1 hour. The solvent was removed, and the device was rinsed thoroughly with dichloromethane and subsequently allowed to air dry for about 10 minutes. The device was placed in a convection oven at 100° C. to remove any residual solvent. The gel content in the coating was then determined using the following equation: % gel content in coating=((mass of coated device after extraction−mass of uncoated device)/(mass of coated device before extraction−mass of uncoated device))× 100. A control experiment on the uncoated woven PLGA 10:90 structure showed no appreciable mass loss in a similar experiment.

Example 4

A pattern was laser cut into a tubular base material to produce self-expanding medical implants. Some of the implants were coated with a support coating made from PGCL cured with HDI, as described in Example 1. Similar to the previous examples, coated implants demonstrated higher RRF and COF properties as compared with uncoated implants.

Example 5

Braided implants having an as-manufactured diameter of 6 mm were manufactured using a PLGA 75:25 copolymer using a manufacturing process similar to that of Example 1. The implants were coated with a support coating made from PLCL 50:50 prepared as follows. A 250 mL round-bottom flask was dried in an oven at 110° C. and cooled to room temperature in a nitrogen atmosphere. The flask was charged with $Sn(Oct)_2$ (11.5 mg), pentaerythritol (204 mg), lactide (30.0 g), and ε-caprolactone (30.0 g), respectively. Subsequently, the flask was equipped with a magnetic stir bar and a three-way valve connected to a nitrogen balloon. The flask was thoroughly degassed under reduced pressure and flushed with nitrogen. The flask was then placed into an oil bath which was preheated to 170° C. The reaction was stirred at 170° C. for 48 h under a nitrogen atmosphere. After cooling to room temperature, the highly viscous liquid obtained was dissolved in approximately 200 mL dichloromethane and precipitated from 1200 mL anhydrous diethyl ether. The solution was decanted and the residual sticky polymer was washed thoroughly with diethyl ether and dried under vacuum. Typically, around 48 g polymer was recovered through the purification. GPC characterization revealed a number average molecular weight (Mn) of 52,500 and a polydispersity index (PDI) of 1.2.

Coated devices were crimped to 1.85 mm in a MSI radial force tester (Model#RX550-100) to obtain RRF and COF values, both measured in mm Hg, at a diameter of 4.5 mm for 6 mm device and at a diameter of 5.5 mm for 7 mm device. Like the implants coated with PGCL described in Example 1, both RRF and COF were found to be directly proportional to the coating weight. The inventors note that both RRF and COF for the coated devices are significantly higher than for uncoated devices. For example, a 7 mm implant having an increase in weight due to the PLCL/HDI coating of about 45% resulted in RRF of about 450 mm Hg and COF of 90 mm Hg, measured at 4.5 mm, while the uncoated device resulted in RRF and COF of 80 mm and 0 mm Hg, respectively.

Example 6

Braided implants having an as-manufactured diameter of 6 mm were manufactured using a PLGA 75:25 copolymer using a manufacturing process similar to that of Example 1. The implants were coated with a support coating made from poly trimethylene carbonate (PTMC) and hexamethylenediisocyante. The PTMC three arm polymer was prepared as follows. A 100 mL round-bottom flask, previously dried under heat and vacuum, was charged with $Sn(Oct)_2$ (20 mg), triethanolamine (298.4 mg) and trimethylene carbonate (30 g) respectively. Subsequently, the flask was equipped with a magnetic stir bar and a three-way valve connected to a nitrogen balloon. The flask was thoroughly degassed under reduced pressure and flushed with nitrogen and then placed into an oil bath which was preheated to 70° C. The oil bath temperature was then increased to 100° C. over 15 minutes. The reaction was stirred at 100° C. for 23 h under a nitrogen atmosphere. After cooling to room temperature, the viscous liquid obtained was dissolved overnight in approximately 50 mL dichloromethane and subsequently precipitated from 550 mL ethanol. The precipitated polymer was stirred for one hour after which the ethanol was decanted. The process of dissolving the polymer in dichloromethane and precipitating in ethanol was repeated. The polymer was then dissolved in dichloromethane, precipitated into 550 mL diethyl ether and stirred for one hour after which time the diethyl ether was decanted. The polymer was then dried under vacuum @ 70° C. for a period of 72 hours. Typically 24 g of polymer was recovered using above process. GPC characterization of the final polymer revealed a number average molecular weight (Mn) of 29 kDa and a polydispersity index (PDI) of 2.0.

An MSI radial force tester (Model#RX550-100) was used to obtain radial resistive force ("RRF") and chronic outward force ("COF"), at a post-crimp diameter of 4.5 mm for PTMC/HDI coated devices. For example, a 6 mm implant having an increase in weight due to the PTMC/HDI support coating of about 50% resulted in RRF of 490 mm Hg and COF of 83 mm Hg, measured at 4.5 mm. PTMC is considered to be a surface-degrading material which does not generate acidic by-products upon degradation.

Example 7

A support coating solution was prepared by dissolving 1.0 g of PLCL 50:50 copolymer (Mn=67 kDa) in 19.875 mL of methlyene chloride. Subsequently, 0.125 mL of hexamethylene diisocyanate is added to the solution, which was then transferred to a 60 mL polypropylene syringe using a 14 gauge needle. No catalyst was added to the support coating solution at any time.

The support coating solution was sprayed onto PLGA 85:15 braided implants. After spray coating, the implants were allowed to dry for up to 60 minutes in a nitrogen atmosphere. The implants were then transferred to a curing oven for a two-step curing process consisting of a first step at 75° C. for 16 hours, followed by a second step at 100° C. for a minimum of 96 hours.

Comparative Example 1

Implants of the present invention were compared to several commercially available, biostable self-expanding implants, namely the VIABAHN® Endoprosthesis (a self-expanding nitinol stent-graft from W.L. Gore & Associates, Inc.), the S.M.A.R.T.® stent (a self-expanding nitinol stent from Cordis Corp.), and the WALLSTENT® Endoprosthesis (a self-expanding steel stent from Boston Scientific Corp.). Specifically, the RRF and COF values of these commercially available implants were measured and compared with 6 mm (having a 127° braid angle) and 7 mm (having braid angles of 127° and 110°) diameter implants made from PLGA 75:25. The PLGA implants were made using a manufacturing process similar to that of Example 1, and coated with a support coating made from PLCL 50:50 copolymer and hexamethylenediisocyanate as described in Example 5 with a coating weight of between 44% and 50% for the 7 mm devices and a weight of 47% to 57% for the 6 mm devices. RRF and COF values were measured at post-crimp diameters corresponding to the range of intended target vessel diameters. The results demonstrated that the implants of the present invention are characterized by mechanical properties such as RRF and COF that are comparable to their commercially available metallic counterparts.

Comparative Example 2

Figure 9:
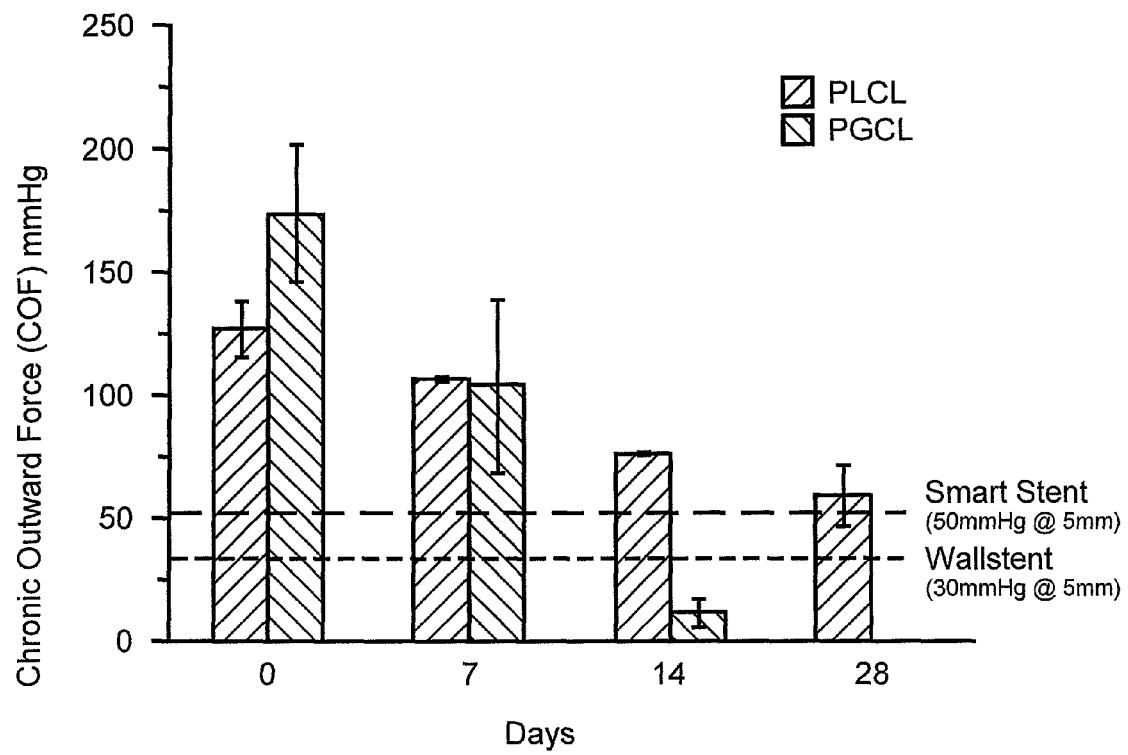
FIG. 9 is a graph of COF values of certain embodiments of the present invention, as well as for known commercial self-expanding stents.

Braided implants having an as-manufactured diameter of 6 mm were manufactured using a PLGA 75:25 copolymer using a manufacturing process similar to that of Example 1. One set of implants were coated with a support coating comprising PGCL 50:50 and hexamethylenediisocyanate, and another set of implants were coated with a support coating comprising PLCL 50:50 and hexamethylenediisocyanate. The implants were deployed into vessel-compliant tubing and maintained at 37° C. under simulated flow conditions for 0, 7, 14, and 28 days. At those time points, the implants were explanted from the tubing, dried overnight, and the COF of the implants was measured at a post-crimp diameter of 4.5 mm. The results are shown in FIG. 9, which demonstrate that the COF for both sets of implants decrease over time, with COF going to zero for the PGCL coated implants as of 28 days. Also shown in FIG. 9 are the COF values measured for the S.M.A.R.T. stent and WALLSTENT Endoprosthesis as described in Comparative Example 1, which are constant because those devices are metallic and do not degrade or relax over time. The inventors believe that the significant decrease in COF over time for the implants of the present invention is an advantage over their metallic stent counterparts because a continuous force applied by implants against surrounding tissue over time may result in chronic irritation and inflammation leading to restenosis.

The present invention provides woven and non-woven self-expanding medical implants for placement within a bodily lumen that have sufficient strength and other mechanical properties that are necessary to effectively treat a variety of medical conditions. While aspects of the invention have been described with reference to example embodiments thereof, it will be understood by those skilled in the art that various changes in form and details may be made therein without departing from the scope of the invention.

We claim:

1. An implantable medical device, comprising:
   a self-expanding tubular structure comprising at least one strand comprising a first polymer characterized by a modulus of elasticity greater than about 1 GPa; and
   a second polymer at least partially and conformally coating said strand, said second polymer being an elastomeric thermoset polymer characterized by a percent elongation to break that is greater than about 150 percent at 37° C.;
   wherein the second polymer increases the mass of said self-expanding tubular structure by at least about 20 percent.

2. The implantable medical device of claim 1, wherein said first polymer is biodegradable.

3. The implantable medical device of claim 2, wherein said first polymer comprises poly(lactic acid co-glycolic acid).

4. The implantable medical device of claim 3, wherein said poly(lactic acid co-glycolic acid) comprises at least about 75 weight percent of lactic acid.

5. The implantable medical device of claim 4, wherein said poly(lactic acid co-glycolic acid) comprises about 85 weight percent of lactic acid.

6. The implantable medical device of claim 4, wherein said second polymer is poly(lactic acid-co-caprolactone) comprising about 50 to 70 weight percent lactic acid, wherein said polymer is cross-linked.

7. The implantable medical device of claim 6, wherein said poly(lactic acid-cocaprolactone) is crosslinked with hexamethylene diisocyanate.

8. The implantable medical device of claim 6, wherein the number average molecular weight (Mn) of said second polymer is greater than about 24,000 Da and less than about 100,000 Da.

9. The implantable medical device of claim 3, wherein said poly(lactic acid co-glycolic acid) comprises up to about 20 weight percent of lactic acid.

10. The implantable medical device of claim 1, wherein said first polymer is characterized by a modulus of elasticity greater than about 6 GPa.

11. The implantable medical device of claim 1, wherein said second polymer is biodegradable.

12. The implantable medical device of claim 11, wherein said second polymer is a random copolymer that is crosslinked.

13. The implantable medical device of claim 11, wherein said second polymer is selected from the group consisting of poly(lactic acid-co-caprolactone), poly(glycolide-co-caprolactone, poly trimethylene carbonate, and poly(lactic acid-co-dioxanone) and wherein said second polymer is cross-linked.

14. The implantable medical device of claim 1, wherein said second polymer is characterized by an elastic segment having a glass transition temperature less than about 5, degree. C.

15. The implantable medical device of claim 1 wherein said self-expanding tubular structure is a braided structure.

16. The implantable medical device of claim 15, wherein said braided structure comprises between 16 and 48 strands.

17. The implantable medical device of claim 16, wherein said strands form an average braid angle of between about 90 degrees and about 135 degrees.

18. The implantable medical device of claim 17, wherein said strands form an average braid angle of between about 110 degrees and about 135 degrees.

19. The implantable medical device of claim 1, further comprising a therapeutic agent within at least one of said first polymer material and said second polymer material.

20. The implantable medical device of claim 1, wherein the second polymer increases the mass of said self-expanding tubular structure by at least about 30 percent.

21. The implantable medical device of claim 1, further comprising a third polymer at least partially coating said second polymer.

22. The implantable medical device of claim 21, further comprising a therapeutic agent within said third polymer.

23. The implantable medical device of claim 1, wherein said second polymer comprises a first segment having a Tg less than about 5.degree. C. and a second segment that is harder than the first segment.

24. The implantable medical device of claim 1, wherein said self expanding tubular structure has a first end and a second end.

25. An implantable medical device, comprising:
a self-expanding tubular structure comprising:
- at least one biodegradable strand comprising poly(lactic acid-co-glycolic acid) comprising at least 75 weight percent of lactic acid; and
- poly(lactic acid-co-caprolactine) at least partially coating said strand;
- wherein said poly9lactic acid-co-caprolactone) is cross-linked and has a number average molecular weight (Mn) greater than 30,000 Da;
    - wherein said poly(lactic acid co-caprolactone) increases the mass of said self-expanding tubular structure by at least 24 percent;
    - wherein said self-expanding tubular structure is a braided structure comprising between 16 and 48 strands forming an average braid angle of between 110 degrees and 135 degrees.

* * * * *